(12) United States Patent
Takahashi

(10) Patent No.: US 9,353,148 B2
(45) Date of Patent: *May 31, 2016

(54) METHOD FOR PRODUCING PEPTIDE

(71) Applicant: AJINOMOTO CO., INC., Chuo-ku (JP)

(72) Inventor: Daisuke Takahashi, Yokkaichi (JP)

(73) Assignee: AJINOMOTO CO., INC., Chuo-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/089,895

(22) Filed: Nov. 26, 2013

(65) Prior Publication Data

US 2014/0080999 A1   Mar. 20, 2014

Related U.S. Application Data

(63) Continuation of application No. PCT/JP2012/064073, filed on May 31, 2012.

(30) Foreign Application Priority Data

May 31, 2011 (JP) .................. 2011-122943

(51) Int. Cl.
| | | |
|---|---|---|
| C07K 5/04 | (2006.01) | |
| C03B 19/12 | (2006.01) | |
| C07K 1/06 | (2006.01) | |
| C07C 229/08 | (2006.01) | |
| C07K 1/02 | (2006.01) | |
| C07C 227/18 | (2006.01) | |
| C07K 1/04 | (2006.01) | |

(52) U.S. Cl.
CPC .............. *C07K 1/061* (2013.01); *C07C 227/18* (2013.01); *C07C 229/08* (2013.01); *C07K 1/02* (2013.01); *C07K 1/062* (2013.01); *C07K 1/045* (2013.01); *Y02P 20/55* (2015.11)

(58) Field of Classification Search
None
See application file for complete search history.

(56) References Cited

U.S. PATENT DOCUMENTS

| | | |
|---|---|---|
| 2009/0299103 A1 | 12/2009 | Chiba et al. |
| 2010/0029904 A1 | 2/2010 | Chiba et al. |
| 2010/0240867 A1 | 9/2010 | Takahash |
| 2010/0249374 A1 | 9/2010 | Takahash |
| 2010/0261876 A1* | 10/2010 | Bray et al. .................... 530/324 |
| 2011/0160433 A1 | 6/2011 | Takahash |
| 2012/0059149 A1 | 3/2012 | Takahash |
| 2012/0108788 A1 | 5/2012 | Chiba et al. |

FOREIGN PATENT DOCUMENTS

| | | | | |
|---|---|---|---|---|
| JP | 2000-044493 A | 2/2000 | | |
| WO | WO03/062266 | * | 7/2003 | .............. C07K 7/08 |
| WO | WO 2006/104166 A1 | 10/2006 | | |
| WO | WO 2007/034812 A1 | 3/2007 | | |
| WO | WO 2007/122847 A1 | 11/2007 | | |
| WO | WO 2010/104169 A1 | 9/2010 | | |
| WO | WO 2010/113939 A1 | 10/2010 | | |
| WO | WO 2011/078295 A1 | 6/2011 | | |
| WO | WO 2012/029794 A1 | 3/2012 | | |

OTHER PUBLICATIONS

Tamiaki et al., A Novel Protecting Group for Constructing Combinatorial Peptide Libraries, Bull. Chem. Soc. Jpn., 74, 733-738, 2001.*
Toma and Tamiaki, Japanese Publication 2000-044493, published Feb. 15, 2000.*
Tana et al., A practical solution-phase synthesis of an antagonistic peptide of TNF—a based on hydrophobic tag strategy, Chem. Commun., 2010, 46, 8219-8221.*
Watanabe et al., Cyclopentyl Methyl Ether as a New and Alternative Process Solvent, Org Proc. Res & Dev. 2007, 11, 251-258.*
"A new solvent for green chemistry," published online Jan. 12, 2011, http://manufacturingchemist.com.*
Eggen et al., A novel method for repetitive peptide synthesis in solution without isolation of intermediates, Jl. Peptide Sci, 11:633-641 (2005).*
U.S. Appl. No. 14/089,853, filed Nov. 26, 2013, Takahashi.
International Search Report issued Sep. 4, 2012 in PCT/JP2012/064073.
Hitoshi Tamiaki, et al., "A Novel Protecting Group for Constructing Combinatorial Peptide Libraries" Bull. Chem. Soc. Jpn. vol. 74, No. 4, 2001, pp. 733-738.
Daisuke Takahashi, "AJIPHASE—A New approach for liquid phase peptide synthesis (LPPS) system using soluble and precipitation support anchors" Proceedings of the 48th Japanese Peptide Symposium, Sep. 2011, pp. 25 [0-03].
Daisuke Takahashi, "AJIPHASE, Development of a Novel-Liquid Phase Peptide Synthesis (LPPS) on Anchors Bearing a Long Aliphatic Chain" The Japanese Society for Process Chemistry, Dec. 2011, pp. 36-38, with an English Abstract.
Daisuke Takahashi, et al., "Development of an efficient liquid-phase peptide synthesis protocol using a novel fluorene-derived anchor support compound with Fmoc chemistry; AJIPHASE" Tetrahedron Letters, vol. 53. No. 15, Feb. 2012, pp. 1936-1939.
Daisuke Takahashi, et al., "AJIPHASE: Chosa Shibozoku Anchor o Riyo shita Shinki na Koritsuteki Ekiso Peptide Goseiho no Kaihatsu to Oyo" Gene & Medicine MOOK, No. 21, Mar. 2012, pp. 54-60, corresponds to AX and AZ.
Daisuke Takahashi, et al., "Novel diphenylmethyl-Derived Amide Protecting Group for Efficient Liquid-Phase Peptide Synthesis: AJIPHASE" Organic Letters, American Chemical Society, vol. 14, No. 17, 2012, pp. 4514-4517.
U.S. Appl. No. 14/244,433, filed Apr. 3, 2014, Takahashi.
D. Takahashi, et al., Tetrahedron Letters, vol. 53, pp. 1936-1939 (2012).

* cited by examiner

*Primary Examiner* — Satyanarayana R Gudibande
(74) *Attorney, Agent, or Firm* — Oblon, McClelland, Maier & Neustadt, L.L.P.

(57) ABSTRACT

The present invention provides a production method of a protected amino acid, protected peptide or peptide, including precipitation and solid-liquid separation of C-protected amino acid or C-protected peptide in a solvent containing water-containing acetonitrile, after removing the N-terminal protecting group from N-protected C-protected amino acid or N-protected C-protected peptide wherein the C-terminal carboxy group is protected by an anchor group.

21 Claims, No Drawings

METHOD FOR PRODUCING PEPTIDE

CROSS REFERENCE TO RELATED APPLICATIONS

This application is a Continuation Application of International Patent Application No. PCT/JP2012/064073, filed on May 31, 2012, and claims priority to Japanese Patent Application No. 2011-122943, filed on May 31, 2011.

TECHNICAL FIELD OF THE INVENTION

The present invention relates to a method capable of obtaining an object peptide with a high purity and a high yield by a convenient operation omitting an isolation and purification operation of an intermediate as much as possible, which is suitable for industrial production.

BACKGROUND OF THE INVENTION

As a production method of peptide besides a solid phase method and a liquid phase method, a production method using a protecting group (hereinafter to be also referred to as an anchor group) permitting a reaction in a homogeneous liquid phase, and, after changing the solvent composition after the reaction, performing isolation and purification merely by filtration and washing (hereinafter to be also referred to as an anchor method) has recently been proposed. The anchor method is a production method of peptide, wherein, in peptide synthesis and the like, a particular compound that shows reversible changes between a dissolved state and an undissolved (precipitated) state according to the changes of the solvent composition is used as a compound (anchor) that forms an anchor group for protecting the C-terminal and/or a side chain functional group of amino acid or peptide. Here, the anchor group means a protecting group that binds to a reactive substrate to make the substrate soluble in nonpolar solvents and capable of reaction in a liquid phase, and that precipitates on addition of a polar solvent to enable solid-liquid separation, thus showing both reactivity and convenience of working up. The anchor means a compound for forming an anchor group.

For example, patent document 1 and non-patent document 1 each disclose a method of using 3,4,5-tri(n-octadecyloxy)benzyl alcohol as an anchor for carboxy group and the like. In addition, patent documents 2-4 each disclose anchors such as 3,5-di(docosyloxy)benzyl alcohol, 2,4-di(docosyloxy)benzyl alcohol, trityl type compound and the like.

The present inventors have also developed a particular diphenylmethane compound (patent document 5) and a fluorene compound (patent document 6) as an anchor usable for the anchor method.

DOCUMENT LIST

Patent Documents patent document 1: JP-A-2000-44493
patent document 2: WO2006/104166
patent document 3: WO2007/034812
patent document 4: WO2007/122847
patent document 5: WO2010/113939
patent document 6: WO2010/104169

Non-Patent Document non-patent document 1: Bull. Chem. Soc. Jpn 74, 733-738 (2001)

SUMMARY OF THE INVENTION

Problems to be Solved by the Invention

The above-mentioned anchor method is a useful method in the organic synthetic methods such as peptide synthesis and the like, which shows advantages of both the solid phase reaction and the liquid phase reaction, such as convenient working up and possible scaling up, and draws attention from an industrial aspect. However, when sequential multistep synthetic reactions are needed such as in the peptide synthesis and the like, isolation and purification operations of concentration, precipitation by poor solvent, filtration, washing and drying need to be repeated in each step, so that undesirable side reactions such as by-production of a double-hit compound due to the residual amino acid and the like will not occur in the next step. Since the high number of operation steps requires a large amount of time and cost, industrialization is prevented. Here, the double-hit compound means a peptide wherein one extra amino acid residue has been further inserted into the object peptide.

The present invention has been made in view of the above-mentioned problems specific to the peptide synthesis by conventional anchor methods, and aims to provide a convenient and industrially useful production method of peptide, which incorporates a step that can be performed successively in one pot by omitting isolation and purification operations of an intermediate as much as possible.

Means of Solving the Problems

The present inventors have found that, after condensation of an amino acid or peptide having an anchor group as a C-terminal carboxy-protecting group and an amino acid or peptide having an N-terminal amino group temporarily protected by a protecting group (hereinafter to be also referred to as a temporary protecting group), the steps up to the removing step of the temporary protecting group can be successively performed in one pot by omitting a set of isolation and purification operations of concentration, precipitation, filtration, washing and drying. In the production method of a peptide of the present invention, a free N-terminal amino group is formed by removing the temporary protecting group rather than an anchor group, and the C-terminal carboxy group of a new amino acid or peptide is reacted with the free N-terminal amino group to elongate the peptide chain. To distinguish from an anchor group, therefore, a protecting group that temporarily protects the N-terminal amino group is called a "temporary protecting group" in the present specification.

To perform the above-mentioned one-pot step repeatedly and efficiently, complete removal of residual amino acid that causes side reactions is necessary. The present inventors have found that precipitation and solid-liquid separation by the addition of a solvent containing water-containing acetonitrile after removing the above-mentioned temporary protecting group can completely remove of the residual amino acid from the condensation product, which resulted in the completion of the present invention. The present invention is as follows.

[1] A method of producing a protected amino acid or protected peptide, comprising:
(1) removing a N-terminal protecting group from (a) an N-protected C-protected amino acid or (b) an N-protected C-protected peptide, to obtain (c) a C-protected amino acid or (d) a C-protected peptide,
wherein a C-terminal carboxy group of said (a) N-protected C-protected amino acid or said (b) N-protected C-protected peptide is protected by an anchor group derived from an anchor which is soluble in a halogenated solvent or an ether solvent, and insoluble in apolar solvent, and which has a molecular weight of not less than 300, without isolating said (a) N-protected C-protected amino acid or said (b) N-protected C-protected peptide from a reaction solution comprising said anchor and an N-protected amino acid or an N-protected peptide;
(2) precipitating said (c) C-protected amino acid or said (d) C-protected peptide in a solvent comprising a water-acetonitrile mixture, wherein said water-acetonitrile mixture comprises and 60 to 95% v/v acetonitrile, based on the total volume of said mixture, after said (1) removing; and
(3) obtaining said C-protected amino acid or said C-protected peptide by solid-liquid separation.

[2] A method of producing a peptide, comprising:
(1) condensing an N-terminal amino group of (a) a C-protected amino acid or a (b) C-protected peptide, with a C-terminal carboxy group of (c) an N-protected amino acid or (d) an N-protected peptide in a solvent to obtain a reaction solution which comprises an (e) N-protected C-protected peptide,
wherein a C-terminal carboxy group of said (a) C-protected amino acid or said (b) C-protected peptide is protected by an anchor group derived from an anchor which is soluble in a halogenated solvent or an ether solvent, insoluble in a polar solvent, and which has a molecular weight of not less than 300;
(2) removing the N-terminal protecting group of said (e) N-protected C-protected peptide in said reaction solution, without isolating said N-protected C-protected peptide, to obtain (b') a C-protected peptide, wherein when said condensing is conducted with said (b) C-protected peptide, then said (b) C-protected peptide and said (b') C-protected peptide are different; and
(3) precipitating said C-protected peptide in a solvent comprising a water-acetonitrile mixture, wherein said water-acetonitrile mixture comprises and 60 to 95% v/v acetonitrile, based on the total volume of said mixture, after said (2) removing; and
(4) obtaining said C-protected peptide by solid-liquid separation.

[3] The method according to [2], further comprising:
(5) removing the C-terminal anchor group of said (b') C-protected peptide after said (4) obtaining.

[4] The method according to [2], wherein said anchor which is soluble in a halogenated solvent or an ether solvent, insoluble in a polar solvent, and has a molecular weight of not less than 300 is a compound represented by formula (I):

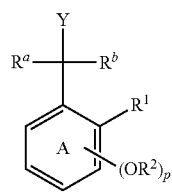

(I)

Wherein:
$R^1$ is a hydrogen atom or, when $R^b$ is a group represented by the following formula (a), optionally forms a single bond together with $R^3$ to form a fluorene ring together with ring A and ring B;

each $R^2$ is independently an organic group having an aliphatic hydrocarbon group;

p is an integer of 1 to 4;

ring A optionally further has, in addition to $OR^2$, a substituent selected from the group consisting of a halogen atom, a $C_{1-6}$ alkyl group optionally substituted by a halogen atom, and a $C_{1-6}$ alkoxy group optionally substituted by a halogen atom;

$R^a$ is a hydrogen atom, or a phenyl group optionally substituted by a halogen atom; and $R^b$ is a hydrogen atom, or a group represented by formula (a):

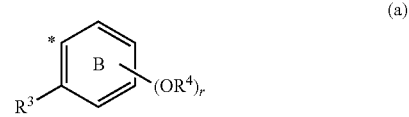

(a)

wherein:
* indicates the position of binding to the remainder of the molecule;

r is an integer of 0 to 4;

each $R^4$ is independently an organic group having an aliphatic hydrocarbon group;

$R^3$ is a hydrogen atom, or optionally forms a single bond together with $R^1$ to form a fluorene ring together with ring A and ring B; and ring B optionally further has, in addition to $OR^4$, a substituent selected from the group consisting of a halogen atom, a $C_{1-6}$ alkyl group optionally substituted by a halogen atom, and a $C_{1-6}$ alkoxy group optionally substituted by a halogen atom; and Y is a hydroxy group, a halogen atome, or NHR, wherein R is a hydrogen atom, an alkyl group or an aralkyl group.

[5] The method according to [4], wherein, in formula (I), Y is a hydroxy group, $R^1$ is a hydrogen atom, $R^2$ and/or $R^4$ are/is aliphatic hydrocarbon group(s) having 5 to 60 carbon atoms, p is an integer of 1 to 3, and r is an integer of 0-2.

[6] The method according to [4], wherein, in formula (I), Y is a hydroxy group, $R^a$, $R^b$, and $R^1$ are each a hydrogen atom, $R^2$ is an aliphatic hydrocarbon group having 5 to 60 carbon atoms, and p is an integer of 1 to 3.

[7] The method according to [4], wherein, in formula (I), Y is a hydroxy group, $R^a$, $R^b$, and $R^1$ are each a hydrogen atom, $R^2$ is an alkyl group having 10 to 40 carbon atoms, and p is 2 or 3.

[8] The method according to [4], wherein, in formula (I), Y is a hydroxy group, $R^a$, $R^b$, and $R^1$ are each a hydrogen atom, $R^2$ is an alkyl group having 12 to 30 carbon atoms, and p is 2 or 3.

[9] The method according to [4], wherein the compound represented by formula (I) is a compound selected from the group consisting of:
  3,4,5-tri(octadecyloxy)benzyl alcohol,
  2,4-di(docosyloxy)benzyl alcohol,
  4-methoxy-2-[3',4',5'-tri(octadecyloxy)benzyloxy]benzyl alcohol,
  4-methoxy-2-[3',4',5'-tri(octadecyloxy)cyclohexylmethyloxy]benzyl alcohol,
  2-methoxy-4-[3',4',5'-tri(octadecyloxy)cyclohexylmethyloxy]benzyl alcohol,
  4-[3',4',5'-tri(octadecyloxy)cyclohexylmethyloxy]benzyl alcohol,
  3,5-dimethoxy-4-[3',4',5'-tri(octadecyloxy)cyclohexylmethyloxy]benzyl alcohol,
  2,4-di(dodecyloxy)benzyl alcohol,
  3,4,5-tri(octadecyloxy)benzylamine,
  bis(4-docosyloxyphenyl)methanol, and
  bis(4-docosyloxyphenyl)methylamine.

[10] The method according to [2], wherein said mixture comprises acetonitrile in an amount of 70 v/v % to 90 v/v % based on the total volume of said mixture.

[11] The method according to [2], wherein said mixture comprises acetonitrile in an amount of 75 v/v % to 85 v/v % based on the total volume of said mixture.

[12] The method according to [2], wherein said mixture comprises acetonitrile in an amount of 80 v/v % based on the total volume of said mixture.

[13] The method according to [2], wherein said solvent comprising a water-acetonitrile mixture is a mixed solvent of said water-acetonitrile mixture, and at least one solvent selected from the group consisting of methanol, ethanol, dimethylformamide, propionitrile, dimethyl sulfoxide, acetone, dichloromethane, chloroform, tetrahydrofuran, cyclopentyl methyl ether, and ethyl acetate.

[14] The method according to [2], wherein said solvent is said water-acetonitrile mixture.

[15] The method according to [2], wherein said amino-protecting group of said (c) N-protected amino acid or said (d) N-protected peptide is a 9-fluorenylmethyloxycarbonyl group, a tert-butoxycarbonyl group, or a benzyloxycarbonyl group.

[16] A method of producing a peptide by successively immobilizing-protecting a C-terminal of an amino acid or peptide and elongating an N-terminal of an amino acid or peptide, comprising:
  after deprotection of a peptide, precipitating said peptide in a polar solvent comprising a water-acetonitrile mixture.

Effect of the Invention

According to the production method of peptide of the present invention, residual amino acid and the like can be effectively removed by merely performing precipitating by a solvent containing water-containing acetonitrile and solid-liquid separation, after removing a temporary N-terminal amino group-protecting group of an amine component used for a condensation step (amino acid or peptide having an anchor as a C-terminal carboxy group-protecting group). As a result, for example, a condensation step of the amine component and N-terminal amino group with an amino acid or peptide protected by a temporary protecting group, and the subsequent step for removing the temporary protecting group can be successively performed in one pot with a high yield and a high purity, without isolation and purification operations of an intermediate. Therefore, a convenient and efficient production method of peptide, which is suitable for industrial production, can be provided.

DESCRIPTION OF EMBODIMENTS

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the present specification are hereby incorporated by reference so as to describe and disclose constructed products and methodology described in, for example, publications usable in relation to the described invention.

An amino acid which is a constitutional unit of a peptide produced by the method of the present invention is a compound having an amino group and a carboxy group in the same molecule, and may be a natural amino acid or non-natural amino acid, and an L form, a D form or a racemate. A peptide is synthesized by repeating a dehydration condensation step (condensation step) of an amino group of an amino acid component and a carboxy group of other amino acid component, according to the amino acid sequence of the peptide. Of the two amino acid components involved in the formation of the peptide bond, a component providing an amino group is hereinafter sometimes referred to as an amine component, and a component providing a carboxy group as an acid component.

The temporary protecting group of the N-terminal amino group of an acid component to be used for the condensation step in the present invention is, for example, a 9-fluorenylmethyloxycarbonyl group (hereinafter to be also referred to as Fmoc group), a tert-butoxycarbonyl group (hereinafter to be also referred to as Boc group) or a benzyloxycarbonyl group (hereinafter to be also referred to as Cbz group), and it is preferably an Fmoc group or a Boc group.

In the present specification, the "N-protected amino acid" or "N-protected peptide" means an amino acid or peptide wherein an N-terminal amino group thereof is protected by a temporary protecting group and a carboxy group is not protected.

In the present specification, the "C-protected amino acid" or "C-protected peptide" means an amino acid or peptide wherein, the C-terminal carboxy group thereof is protected by forming an anchor group by condensing with an anchor soluble in halogenated solvents or ether solvents, insoluble in polar solvents and having a molecular weight of not less than 300 (e.g., benzyl compound, diphenylmethane compound or fluorene compound), and the N-terminal amino group is not protected.

In the present specification, the "N-protected C-protected amino acid" or "N-protected C-protected peptide" means the above-mentioned "C-protected amino acid" or "C-protected peptide" wherein the N-terminal amino acid is protected by a temporary protecting group.

Examples of the halogenated solvent in the present invention include halogenated hydrocarbons such as chloroform, dichloromethane, 1,2-dichloroethane, chlorobenzene and the like. The halogenated solvent may be a mixed solvent of two or more kinds. Among the halogenated solvents, chloroform and dichloromethane are particularly preferable.

Examples of the ether solvent in the present invention include 1,4-dioxane, cyclopentyl methyl ether (hereinafter sometimes to be referred to as CPME), tetrahydrofuran (hereinafter sometimes to be referred to as THF) and the like. The ether solvent may be a mixed solvent of two or more kinds. Among the ether solvents, CPME and THF are particularly preferable.

Examples of the polar solvent in the present invention include methanol, ethanol, isopropanol, acetonitrile, propionitrile, dimethylformamide (hereinafter sometimes to be referred to as DMF), dimethylacetamide, dimethyl sulfoxide, water and the like, and a mixed solvent of two or more kinds of these.

The "water-containing acetonitrile" in the "solvent containing water-containing acetonitrile" means a mixed solvent of acetonitrile and water. The lower limit of the content of acetonitrile in the water-containing acetonitrile is preferably 60 v/v %, more preferably 70 v/v %, and further preferably 75 v/v %. On the other hand, the upper limit of the content of acetonitrile in the water-containing acetonitrile is preferably 95 v/v %, more preferably 90 v/v %, and further preferably 85 v/v %. A particularly preferable content of acetonitrile in the water-containing acetonitrile is 80 v/v %. In the present specification, for example, water-containing acetonitrile having an acetonitrile content of 80 v/v % is sometimes indicated as "80% water-containing acetonitrile".

The "solvent containing water-containing acetonitrile" may be the above-mentioned "water-containing acetonitrile" alone, or a mixed solvent with other organic solvent. While such other organic solvent is not particularly limited as long as it can remove the residual amino acid and the like by mixing with water-containing acetonitrile, alcohol solvents such as methanol, ethanol and the like, amide solvents such as DMF and the like, nitrile solvents (excluding acetonitrile) such as propionitrile and the like, halogenated solvents, ether solvents, dimethyl sulfoxide, acetone, ethyl acetate and the like can be mentioned.

One embodiment of the anchor soluble in halogenated solvents or ether solvents, insoluble in polar solvents and having a molecular weight of not less than 300 in the present invention is a compound represented by the following formula (I). Among such compounds, one having a molecular weight of not less than 400 is preferable.

The formula (I):

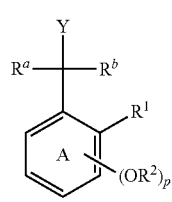

wherein $R^1$ is a hydrogen atom or, when $R^b$ is a group represented by the following formula (a), optionally shows a single bond together with $R^3$ to form a fluorene ring together with ring A and ring B;

$R^2$ in the number of p is each independently an organic group having an aliphatic hydrocarbon group;

p is an integer of 1 to 4;

ring A optionally further has, in addition to $OR^2$ in the number of p, a substituent selected from the group consisting of a halogen atom, a $C_{1-6}$ alkyl group optionally substituted by a halogen atom, and a $C_{1-6}$ alkoxy group optionally substituted by a halogen atom;

$R^a$ is a hydrogen atom, or a phenyl group optionally substituted by a halogen atom; and $R^b$ is a hydrogen atom, or a group represented by the formula (a):

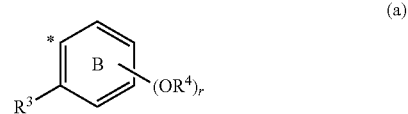

wherein * is a binding site;

r is an integer of 0 to 4;

$R^4$ in the number of r is each independently an organic group having an aliphatic hydrocarbon group;

$R^3$ is a hydrogen atom, or optionally shows a single bond together with $R^1$ to form a fluorene ring together with ring A and ring B; and ring B optionally further has, in addition to $OR^4$ in the number of r, a substituent selected from the group consisting of a halogen atom, a $C_{1-6}$ alkyl group optionally substituted by a halogen atom, and a $C_{1-6}$ alkoxy group optionally substituted by a halogen atom; and Y is a hydroxy group, NHR(R is a hydrogen atom, an alkyl group or an aralkyl group) or a halogen atom.

The anchor represented by the above-mentioned formula (I) is bound to a compound intended to be protected. That is, an anchor wherein Y is a hydroxy group, an —NHR group or a halogen atom protects a compound by condensing with a carboxy group on the C-terminal of amino acid or peptide and the like.

In the present specification, as the "alkyl group" for R, a straight or branched $C_{1-30}$ alkyl group can be mentioned. It is preferably a $C_{1-10}$ alkyl group, more preferably a $C_{1-6}$ alkyl group. Specific preferable examples include methyl, ethyl, propyl, isopropyl, butyl, isobutyl, sec-butyl, tert-butyl and the like, and methyl and ethyl are particularly preferable.

In the present specification, as the "aralkyl group" for R, a $C_{7-30}$ aralkyl group can be mentioned. It is preferably a $C_{7-20}$ aralkyl group, more preferably a $C_{7-16}$ aralkyl group ($C_{6-10}$ aryl-$C_{1-6}$ alkyl group). Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

As R, a hydrogen atom, a $C_{1-6}$ alkyl group or a $C_{7-16}$ aralkyl group is preferable, a hydrogen atom, methyl, ethyl or benzyl is more preferable, and a hydrogen atom is particularly preferable.

In the present specification, the "halogen atom" is a fluorine atom, a chlorine atom, a bromine atom or an iodine atom. In the present specification, as the "halogen atom" for Y, a chlorine atom, a bromine atom or an iodine atom is preferable, and a bromine atom is more preferable.

In the present specification, the "organic group having an aliphatic hydrocarbon group" for $R^2$ or $R^4$ is a monovalent organic group having an aliphatic hydrocarbon group in a molecule structure thereof.

The "aliphatic hydrocarbon group" in the "organic group having an aliphatic hydrocarbon group" is a straight or branched saturated or unsaturated aliphatic hydrocarbon group, preferably an aliphatic hydrocarbon group having 5 or more carbon atoms, more preferably an aliphatic hydrocarbon group having 5 to 60 carbon atoms, further preferably an aliphatic hydrocarbon group having 5 to 30 carbon atoms, particularly preferably an aliphatic hydrocarbon group 10 to 30 carbon atoms.

The moiety of the "aliphatic hydrocarbon group" in the "organic group having an aliphatic hydrocarbon group" is not particularly limited, and may be present at the terminal (monovalent group), or other site (for example, divalent group).

Examples of the "aliphatic hydrocarbon group" include monovalent groups such as an alkyl group, a cycloalkyl group, an alkenyl group, a cycloalkenyl group, an alkynyl group and the like, and divalent groups derived therefrom, preferably monovalent groups such as a methyl group, an ethyl group, a propyl group, an isopropyl group, a butyl group, an isobutyl group, a sec-butyl group, a tert-butyl group, a pentyl group, a hexyl group, an octyl group, a decyl group, a dodecyl group, a lauryl group, a tridecyl group, a myristyl group, a cetyl group, a stearyl group, an arachyl group, a behenyl group, an oleyl group, an isostearyl group and the like, and divalent groups derived therefrom.

The moiety other than the "aliphatic hydrocarbon group" of the "organic group having an aliphatic hydrocarbon group" can be set freely. For example, it may have a moiety such as —O—, —S—, —COO—, —OCONH—, —CONH—, a hydrocarbon group (monovalent group or divalent group) and the like as a linker. Examples of the "hydrocarbon group" include an aliphatic hydrocarbon group, an aromatic-aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferable and, for example, vinyl, 1-propenyl, allyl, isopropenyl, butenyl, isobutenyl and the like can be mentioned. As the "alkynyl group", a $C_{2-6}$ alkynyl group and the like are preferable and, for example, ethynyl, propargyl, 1-propynyl and the like can be mentioned. As the "cycloalkyl group", a $C_{3-6}$ cycloalkyl group and the like are preferable and, for example, cyclopropyl, cyclobutyl, cyclopentyl, cyclohexyl and the like can be mentioned. For example, the "aryl group" is preferably a $C_{6-14}$ aryl group and the like and, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is more preferable, and benzyl is particularly preferable. The "hydrocarbon group" may be substituted by a substituent selected from a halogen atom (a chlorine atom, a bromine atom, a fluorine atom, an iodine atom), an alkyl group having 1 to 6 carbon atoms and optionally substituted by one or more halogen atoms, an oxo group and the like.

In the "organic group having an aliphatic hydrocarbon group" constituting the $OR^2$ group or $OR^4$ group in the above-mentioned formula (I), plural "aliphatic hydrocarbon groups" may be present by branching and the like. When plural "aliphatic hydrocarbon groups" are present in the "organic group having an aliphatic hydrocarbon group", they may be the same or different.

In the "organic group having an aliphatic hydrocarbon group" for $R^2$ or $R^4$ in the above-mentioned formula (I), the lower limit of the total carbon number is preferably 5, more preferably 10, further preferably 12, still more preferably 14, especially preferably 16, and particularly preferably 20. On the other hand, in the "organic group having an aliphatic hydrocarbon group" for $R^2$ or $R^4$, the upper limit of the total carbon number is preferably 200, more preferably 150, further preferably 120, still more preferably 100, especially preferably 80, particularly preferably 60, particularly further preferably 40, and most preferably 30. The higher the carbon number, the better the crystallinity of the compound represented by the formula (I) in a polar solvent becomes, even when the peptide chain is a long chain.

Specific preferable examples of the "$OR^2$" group or "$OR^4$" group include dodecyloxy, cetyl oxy, octadecyloxy, docosyloxy, docosyloxy-dodecyloxy, triacontyloxy and the like. The "$OR^2$" group or "$OR^4$" group is present in a total number of p or r (p is an integer of 1 to 4 and r is an integer of 0 to 4), p is preferably 2 or 3, and r is preferably an integer of 0 to 2.

Specific preferable examples of the substituent optionally present in ring A or ring B in the above-mentioned formula (I) include a $C_{1-6}$ alkoxy group (e.g., a $C_{1-4}$ alkoxy group such as methoxy, ethoxy, propoxy, isopropoxy, butoxy, isobutoxy, sec-butoxy, tert-butoxy and the like), a $C_{1-6}$ alkyl group optionally substituted by one or more halogens (e.g., a $C_{1-6}$ alkyl group such as methyl, ethyl, propyl, isopropyl, butyl, isobutyl, sec-butyl, tert-butyl, pentyl, hexyl and the like, a halogen-substituted $C_{1-6}$ alkyl group such as trifluoromethyl, trichloromethyl and the like), and a halogen atom. Of these, a $C_{1-6}$ alkoxy group is preferable.

A preferable embodiment of the anchor represented by the above-mentioned formula (I) is a compound of the formula (I), wherein Y is a hydroxy group;

$R^1$ is a hydrogen atom;

$R^2$ and/or $R^4$ are/is an aliphatic hydrocarbon group having 5 to 60 carbon atoms;

p is an integer of 1 to 3; and r is an integer of 0 to 2.

Another preferable embodiment of the anchor represented by the above-mentioned formula (I) is a compound of the formula (I), wherein Y is a hydroxy group;

$R^a$, $R^b$, and $R^1$ are each a hydrogen atom;

$R^2$ is an aliphatic hydrocarbon group having 5 to 60 carbon atoms; and p is an integer of 1 to 3.

Another preferable embodiment of the anchor represented by the above-mentioned formula (I) is a compound of the formula (I), wherein Y is a hydroxy group;

$R^a$, $R^b$, and $R^1$ are each a hydrogen atom;

$R^2$ is an alkyl group having 10 to 40 carbon atoms; and p is 2 or 3.

Another preferable embodiment of the anchor represented by the above-mentioned formula (I) is a compound of the formula (I), wherein Y is a hydroxy group;

$R^a$, $R^b$, and $R^1$ are each a hydrogen atom;

$R^2$ is an alkyl group having 12 to 30 carbon atoms; and p is 2 or 3.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is a benzyl group having 1 to 3 alkoxy groups having 12 to carbon atoms; and
p is an integer of 1 to 3.

Another preferable embodiment of the anchor represented by the above-mentioned formula (I) is a compound of the formula (I), wherein
Y is a hydroxy group;
$R^a$, $R^b$, and $R^1$ are each a hydrogen atom;
$R^2$ is a cyclohexylmethyl group having 1 to 3 alkoxy groups having 12 to 30 carbon atoms; and
p is an integer of 1 to 3.

Preferable examples of the anchor soluble in halogenated solvents or ether solvents, insoluble in polar solvents and having a molecular weight of not less than 300 in the present invention include the following anchors.
3,4,5-tri(octadecyloxy)benzyl alcohol,
2,4-di(docosyloxy)benzyl alcohol,
4-methoxy-2-[3',4',5'-tri(octadecyloxy)benzyloxy]benzyl alcohol,
4-methoxy-2-[3',4',5'-tri(octadecyloxy)cyclohexylmethyloxy]benzyl alcohol,
2-methoxy-4-[3',4',5'-tri(octadecyloxy)cyclohexylmethyloxy]benzyl alcohol,
4-[3',4',5'-tri(octadecyloxy)cyclohexylmethyloxy]benzyl alcohol,
3,5-dimethoxy-4-[3',4',5'-tri(octadecyloxy)cyclohexylmethyloxy]benzyl alcohol,
2,4-di(dodecyloxy)benzyl alcohol,
3,4,5-tri(octadecyloxy)benzylamine,
bis(4-docosyloxyphenyl)methanol,
bis(4-docosyloxyphenyl)methylamine, and
2-(12-docosyloxy-dodecyloxy)-9-(3-fluorophenyl)-9-bromofluorene.

While the production method of the aforementioned anchor is not particularly limited, it can be produced from a starting material compound according to a method known per se (patent documents 1-6, non-patent document 1) or a method analogous thereto. A compound used as a starting material, for example, halide corresponding to the group $R^2$ or $R^4$ in the formula (I) and the like can be obtained as a commercially available product or can be produced by a method known per se or a method analogous thereto.

An amino acid or peptide which is an acid component or an amine component to be used in the present invention often has, in addition to an amino group or carboxy group involved in the formation of a peptide bond, a functional group subjected to a dehydration condensation reaction, such as an amino group, a carboxy group, a hydroxy group and the like. Such functional group is distinguished from an amino group and a carboxy group forming a peptide bond of the main chain, and referred to as a side chain functional group. While the side chain functional group does not need to be always protected as long as it does not impair the gist of the present invention, it is preferably protected by an appropriate protecting group to prevent an undesirable side reaction during peptide bond formation by a dehydration condensation reaction and deprotection of an N-terminal amino groups.

The protecting group of the side chain functional group is subject to a certain limitation on the combination with the N-terminal amino-protecting group, like the C-terminal carboxy-protecting group of the aforementioned amine component. That is, the protecting group of the side chain functional group needs to be maintained until the completion of the desired amino acid sequence, without being removed even under the removing conditions of the temporary protecting group of the N-terminal amino group. The protecting group is not particularly limited as long as the side chain functional group does not cause an undesirable side reaction during formation of the peptide bond by a dehydration condensation reaction and deprotection of the N-terminal amino group.

The protecting group of the side chain functional group is not particularly limited as long as it is stable under the deprotection conditions of the temporary protecting group of the N-terminal amino group. For example, the protecting groups described in PEPTIDE GOUSEI NO KISO TO JIKKENN (basis and experiment of peptide synthesis), published by Maruzen Co., Ltd. (1985), PROTECTIVE GROUPS IN ORGANIC SYNTHESIS, the third edition, published by JOHN WILLY&SONS (1999) and the like can be mentioned.

When the side chain functional group is a carboxy group, an ester-type protecting group, an amide-type protecting group, a hydrazide-type protecting group and the like can be mentioned.

As the ester-type protecting group, substituted or unsubstituted alkyl ester, and substituted or unsubstituted aralkyl ester are preferably used. As the substituted or unsubstituted alkyl ester, methyl ester, ethyl ester, tert-butyl ester, cyclohexyl ester, trichloroethyl ester, phenacyl ester and the like are preferably used. As the substituted or unsubstituted aralkyl ester, benzyl ester, p-nitrobenzyl ester, p-methoxybenzyl ester, diphenylmethyl ester, 9-fluorenylmethyl (Fm) ester, 4-picolyl (Pic) ester and the like are preferably used.

As the amide-type protecting group, unsubstituted amide, primary amide such as N-methylamide, N-ethylamide, N-benzylamide and the like, secondary amide such as N,N-dimethylamide, pyrrolidinylamide, piperidinylamide and the like, and the like are preferably used.

As the hydrazide-type protecting group, unsubstituted hydrazide, N-phenylhydrazide, N,N'-diisopropylhydrazide and the like are preferably used.

Of these, when the N-terminal temporary protecting group is an Fmoc group, ester-type protecting groups which are stable under the deprotection conditions, such as t-butyl ester, substituted or unsubstituted benzyl ester and the like are preferably used, and substituted or unsubstituted benzyl ester is particularly preferably used since synthesis thereof is comparatively easy.

When the side chain functional group is an amino group, a urethane-type protecting group, an acyl-type protecting group, a sulfonyl-type protecting group and the like can be mentioned.

As the urethane-type protecting group, for example, a methoxycarbonyl group, an ethoxycarbonyl group, a tert-butoxycarbonyl (Boc) group, a benzyloxycarbonyl (Cbz) group and the like are used, and a methoxycarbonyl group, an ethoxycarbonyl group, a Boc group and the like are preferable. Of these, when the N-terminal temporary protecting group is an Fmoc group, a Boc group is particularly preferably used since selective deprotection thereof is possible under mild acidic conditions. When the N-terminal temporary protecting group is a Boc group, a Cbz group and a bromobenzyloxycarbonyl group are particularly preferably used.

As the acyl-type protecting group, for example, a formyl group, an acetyl group, a trifluoroacetyl group and the like are preferably used.

As the sulfonyl-type protecting group, for example, a p-toluenesulfonyl (Ts) group, a p-tolylmethanesulfonyl group, a 4-methoxy-2,3,6-trimethylbenzenesulfonyl group and the like are preferably used.

As for side chain functional groups other than those mentioned above, a protecting group stable under the deprotection conditions of the temporary protecting group of the N-terminal amino group can be selected and used.

The side chain functional group can be deprotected as necessary after forming the object peptide bond.

Next, the production method of the present invention is explained. The production method of the present invention is a production method of protected amino acid, protected peptide or peptide, which includes a precipitation step and a solid-liquid separation step by the addition of water-containing acetonitrile after removing the N-terminal temporary protecting group.

The first embodiment of the production method of the present invention is a production method of a protected amino acid or protected peptide, comprising the following steps (1) and (2);
(1) obtaining a C-protected amino acid or C-protected peptide by removing a N-terminal protecting group from an N-protected C-protected amino acid or N-protected C-protected peptide wherein a C-terminal carboxy group is protected by an anchor group derived from an anchor soluble in halogenated solvents or ether solvents, insoluble in polar solvents and having a molecular weight of not less than 300, without isolating from a reaction solution of the aforementioned anchor and an N-protected amino acid or N-protected peptide (N-terminal deprotection step), and
(2) precipitating the C-protected amino acid or C-protected peptide in a solvent containing 60-95% water-containing acetonitrile after step (1), and obtaining same by solid-liquid separation (precipitation and solid-liquid separation step).

The N-protected C-protected amino acid or N-protected C-protected peptide to be used in the above-mentioned step (1) can be produced by the following step (a). In the following, step (a) is first explained before explanation on step (1).
Step (a) (Condensation Step)

In this step, an anchor soluble in halogenated solvents or ether solvents, insoluble in polar solvents and having a molecular weight of not less than 300 is condensed with a C-terminal carboxy group of N-protected amino acid or N-protected peptide in a solvent to give N-protected C-protected amino acid or N-protected C-protected peptide.

While the upper limit of the number of amino acid residues of the N-protected peptide is not particularly limited as long as the N-protected peptide to be used in this step is soluble in a solvent to be used in this step, the number of amino acid residues of N-protected peptide is preferably not more than 100, more preferably not more than 50, still more preferably not more than 30, especially preferably not more than 10, particularly preferably not more than 5.

The condensation reaction is preferably performed by dissolving anchor, N-protected amino acid or N-protected peptide and a catalytic amount of dimethylaminopyridine in a solvent, adding a condensing agent and stirring the mixture.

This step is performed in a solvent that does not influence the reaction. The higher the solubility in the solvent becomes, the more superior the reactivity is expected to be. Therefore, a solvent showing high solubility of the aforementioned N-protected amino acid or N-protected peptide is preferably selected. Specifically, halogenated solvents such as chloroform, dichloromethane, 1,2-dichloroethane and the like; and ether solvents such as 1,4-dioxane, cyclopentyl methyl ether, tetrahydrofuran and the like can be mentioned. Two or more kinds of these solvents may be used in a mixture in an appropriate ratio. In addition, aromatic hydrocarbons such as benzene, toluene, xylene and the like; nitriles (excluding acetonitrile) such as propionitrile and the like; ketones such as acetone, 2-butanone and the like; amides such as N,N-dimethylformamide and the like; sulfoxides such as dimethyl sulfoxide and the like may be mixed at an appropriate proportion with the above-mentioned halogenated solvent and ether solvents as long as the compound to be used for the production method of the present invention can be dissolved. Of these, chloroform, dichloromethane, cyclopentyl methyl ether or tetrahydrofuran is preferable, and chloroform is particularly preferable.

While the concentration of the N-protected amino acid or N-protected peptide in a solution in this step is not particularly limited as long as it is dissolved, it is preferably 1-30 wt %.

The amount of the N-protected amino acid or N-protected peptide to be used in this step can be 1-10 mol, preferably 1-5 mol, per 1 mol of the aforementioned anchor.

When Y in the aforementioned formula (I) is a hydroxy group, an ester bond is formed by adding a condensing agent and, where necessary, a condensation accelerator in a solvent that does not influence the reaction in the presence of a dimethylaminopyridine catalyst.

When Y in the aforementioned formula (I) is an —NHR group, an amide bond is formed by adding a condensing agent in the presence of a condensation accelerator.

When Y in the aforementioned formula (I) is a halogen atom, an ester bond is formed by adding a base such as diisopropylethylamine and the like in a solvent that does not influence the reaction.

As a condensation accelerator, 1-hydroxybenzotriazole (HOBt), ethyl 1-hydroxy-1H-1,2,3-triazole-5-carboxylate (HOCt), 1-hydroxy-7-azabenzotriazole (HOAt), O-(benzotriazol-1-yl)-N,N,N',N'-tetramethyluronium hexafluorophosphate (HBTU), O-(6-chlorobenzotriazol-1-yl)-N,N,N',N'-tetramethyluronium hexafluorophosphate (HCTU) and the like can be mentioned, with preference given to HOBt.

The amount of the condensation accelerator to be used is preferably 0.05-1.5 mol per 1 mol of the aforementioned anchor.

As a condensing agent, dicyclohexylcarbodiimide (DCC), diisopropylcarbodiimide (DIC), N-ethyl-N'-3-dimethylaminopropylcarbodiimide and hydrochloride thereof (EDC HCl), (benzotriazol-1-yloxy)tripyrrolidinophosphonium hexafluorophosphate (PyBop), 0-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluorophosphate (HBTU) and the like can be mentioned.

The amount of the condensing agent to be used is, for example, 1-10 mol, preferably 1-5 mol, per 1 mol of the aforementioned anchor.

While the reaction temperature is not particularly limited as long as the reaction proceeds, it is preferably not less than −10° C., more preferably not less than 0° C., preferably not more than 50° C., more preferably not more than 30° C. The reaction time is, for example, 1-70 hr.
Step (1) (Deprotection Step of N-Terminal)

In this step, the N-terminal temporary protecting group is removed from N-protected C-protected amino acid or N-protected C-protected peptide, without isolating from the reaction solution of the anchor and N-protected amino acid or N-protected peptide. This step may contain a neutralization step after the removing step.

Removal (deprotection) of the N-terminal temporary protecting group of the N-protected C-protected amino acid or N-protected C-protected peptide can be performed by a known method. For example, when the temporary protecting group is an Fmoc group, the deprotection is performed by treating with an organic base, when the temporary protecting group is a Boc group, it is performed by treating with an acid, and when the temporary protecting group is a Cbz group, it is performed by a catalytic reduction and the like. The deprotection is performed in a solvent that does not influence the reaction.

While the organic base usable for the removal of an Fmoc group is not particularly limited, secondary amines such as diethylamine, piperidine, morpholine and the like, tertiary amines such as diisopropylethylamine, dimethylaminopyridine, 1,8-diazabicyclo[5.4.0]-7-undecene (DBU), 1,4-diazabicyclo[2.2.2]octane (DABCO), 1,5-diazabicyclo[4.3.0]-5-nonene (DBN) and the like can be mentioned. Of these, deprotection is performed in a halogenated solvent or ether solvent, DBU and the like are preferable. The amount of the organic base to be used is, for example, 1-100 mol, preferably 1-10 mol, per 1 mol of the aforementioned N-protected C-protected amino acid or N-protected C-protected peptide.

While the acid usable for the removal of a Boc group is not particularly limited, mineral acids such as hydrogen chloride, sulfuric acid, nitric acid and the like, carboxylic acids such as formic acid, trifluoroacetic acid (TFA) and the like, sulfonic acids such as methanesulfonic acid, p-toluenesulfonic acid and the like, or a mixture thereof can be used. As the mixture, for example, hydrogen bromide/acetic acid, hydrogen chloride/dioxane, hydrogen chloride/acetic acid and the like can be mentioned. When an acid other than an aqueous solution is used, for example, when formic acid, methanesulfonic acid and the like are used in a non-aqueous system, for example, it is possible to selectively remove the Boc group while retaining an anchor group, which is a protecting group of carboxy group subject to hydrolysis under acidic conditions. Particularly, water-soluble sulfonic acids which are liquid at ambient temperature such as methanesulfonic acid and the like are preferable since, when they are used in a non-aqueous system, they can quickly progress the reaction at room temperature with a comparatively small amount of use. The amount of the acid to be used is, for example, 1-100 mol, preferably 1-10 mol, per 1 mol of the aforementioned N-protected C-protected amino acid or N-protected C-protected peptide.

While the catalyst usable for the removal of the Cbz group is not particularly limited, for example, palladium and the like can be mentioned. The amount of the catalyst to be used is, for example, not less than 1 part by weight, preferably not less than 5 parts by weight, for example, not more than 50 parts by weight, preferably 30 parts by weight, per 100 parts by weight of the aforementioned N-protected C-protected amino acid or N-protected C-protected peptide.

Examples of the solvent that does not influence the reaction include halogenated solvents such as chloroform, dichloromethane, 1,2-dichloroethane and the like; aromatic hydrocarbons such as toluene, xylene and the like; ether solvents such as diethyl ether, CPME, THF, 1,4-dioxane and the like; and the like, or a mixture thereof, preferably chloroform, dichloromethane and THF.

When the temporary protecting group of the aforementioned N-terminal is an Fmoc group, a neutralization step by the addition of an acid may be incorporated before the next precipitation, solid-liquid separation step, since an excess amount of the organic base used for the deprotection may exhibit an adverse influence on the reaction product during working up such as solvent evaporation and the like.

As an acid to be used for the neutralization step, for example, methanesulfonic acid, trifluoromethanesulfonic acid, benzenesulfonic acid, p-toluenesulfonic anhydride, sulfuric acid, hydrogen chloride and the like can be mentioned. Of these, methanesulfonic acid, trifluoromethanesulfonic acid, and hydrogen chloride are preferable.

The amount of the acid to be used for the neutralization step is, for example, not less than 0.5 mol, preferably not less than 0.9 mol, for example, not more than 10 mol, preferably not more than 5 mol, per 1 mol of the organic base.

While the temperature of the reaction of step (1) is not particularly limited as long as the reaction proceeds, it is preferably not less than −10° C., more preferably not less than 0° C., preferably not more than 50° C., more preferably not more than 30° C. The reaction time of step (1) is, for example, 1-70 hr.

Step (2) (Precipitation and Solid-Liquid Separation Step)

In this step, C-protected amino acid or C-protected peptide obtained in the above-mentioned step (1) is isolated by changing the solvent dissolving the C-protected amino acid or C-protected peptide (e.g., change of solvent composition, change of solvent kind) to allow for precipitation. That is, the deprotection of step (1) is performed under the conditions under which C-protected amino acid or C-protected peptide is dissolved, solvent exchange is performed to precipitate C-protected amino acid or C-protected peptide, and the impurity (free amino acid, free peptide etc.) is removed by solid-liquid separation. Solvent evaporation and the like may be performed before solvent exchange.

As a solvent for exchange, polar solvents such as methanol, acetonitrile and the like can be used. When methanol is used as a solvent for exchange and removal of the solvent is insufficient though residual amino acid can be removed, problems such as transesterification reaction with an anchor group and the like occur during the isolation operation or the following condensation step. Therefore, a drying step needs to be formed to sufficiently remove methanol, which problematically requires much time for industrialization. In addition, it was found that when acetonitrile is used as a solvent for exchange as mentioned below, residual amino acid cannot be sufficiently removed and, when subjected to the next condensation step, a double-hit compound derived from the residual amino acid is by-produced. Moreover, when water is used as a solvent for exchange, the object peptide compound coagulates in a state containing impurities, which makes it difficult to efficiently remove the residual amino acid or peptide. Therefore, to isolate C-protected amino acid or C-protected peptide from the reaction mixture with high purity, or obtain C-protected amino acid or C-protected peptide having a purity sufficient for the successive one-pot reaction consisting of a condensation step and a deprotection step, a solvent containing water-containing acetonitrile needs to be used as a solvent for exchange.

In this step, the lower limit of the content of acetonitrile in water-containing acetonitrile is preferably 60 v/v %, more preferably 70 v/v %, still more preferably 75 v/v %. On the other hand, the upper limit of the content of acetonitrile in water-containing acetonitrile is preferably 95 v/v %, more preferably 90 v/v %, still more preferably 85 v/v %. A particularly preferable content of acetonitrile in water-containing acetonitrile is 80 v/v %.

In this step, the "solvent containing water-containing acetonitrile" may be the above-mentioned "water-containing acetonitrile" alone or a mixed solvent with other organic solvent mentioned above. As other organic solvent, at least one kind of solvent selected from the group consisting of methanol, ethanol, dimethylformamide, propionitrile, dimethyl sulfoxide, acetone, dichloromethane, chloroform, tetrahydrofuran, cyclopentyl methyl ether and ethyl acetate is preferable. The content of the "water-containing acetonitrile" in the "solvent containing water-containing acetonitrile" is not particularly limited as long as amino acids can be removed, and 60 v/v %-100 v/v % is preferable.

The second embodiment of the production method of the present invention is a production method of peptide, comprising the following steps (3) to (5);
(3) condensing an N-terminal amino group of a C-protected amino acid or C-protected peptide wherein a C-terminal carboxy group is protected by an anchor group derived from an anchor soluble in halogenated solvents or ether solvents, insoluble in polar solvents and having a molecular weight of not less than 300, and a C-terminal carboxy group of an N-protected amino acid or N-protected peptide in a solvent to give an N-protected C-protected peptide,
(4) removing the N-terminal protecting group of the N-protected C-protected peptide obtained in step (3) in the reaction solution of step (3), without isolating the N-protected C-protected peptide, to give a C-protected peptide (N-terminal deprotection step), and
(5) precipitating C-protected peptide in a solvent containing 60-95% water-containing acetonitrile after step (4), and obtaining same by solid-liquid separation (precipitation and solid-liquid separation step).

Step (3) (Condensation Step)

In this step, an N-terminal amino group of C-protected amino acid or C-protected peptide and a C-terminal carboxy group of N-protected amino acid or N-protected peptide are condensed under the conditions similar to those in step (a) wherein Y in the aforementioned formula (I) is NHR.

While the upper limit of the number of amino acid residues of the C-protected peptide is not particularly limited as long as the C-protected peptide to be used in this step is soluble in a solvent to be used in this step, the number of amino acid residues of C-protected peptide is preferably not more than 100, more preferably not more than 50, still more preferably not more than 30. While the upper limit of the number of amino acid residues of the N-protected peptide is not particularly limited as long as the N-protected peptide to be used in this step is soluble in a solvent to be used in this step, the number of amino acid residues of N-protected peptide is preferably not more than 100, more preferably not more than 50, still more preferably not more than 30, especially preferably not more than 10, particularly preferably not more than 5.

Step (4) (N-Terminal Deprotection Step)

This step is performed in the same manner as in the deprotection step of N-terminal in step (1).

Step (5) (Precipitation and Solid-Liquid Separation Step)

This step is performed in the same manner as in the precipitation and solid-liquid separation step in step (2).

The above-mentioned steps (3)-(5) may be repeated two times or more to obtain a C-protected peptide having an elongated peptide chain. While the upper limit of the number of amino acid residues of the C-protected peptide having an elongated peptide chain is not particularly limited as long as the C-protected peptide is soluble in the solvent to be used in step (3), the number of the amino acid residues is preferably not more than 200, more preferably not more than 100, more preferably not more than 50.

The production method of the peptide of the present invention can further contain step (6) for removing the C-terminal anchor group of the C-protected peptide after the precipitation step (5).

By the removal (deprotection) of the C-terminal anchor group, the final object product peptide wherein the C-terminal of the peptide is —COOH (e.g., the aforementioned formula (I) wherein Y is a hydroxy group or a halogen atom), or —CONHR (e.g., the aforementioned formula (I) wherein Y is an NHR group) can be obtained.

When an anchor group derived from an anchor of the aforementioned formula (I) wherein Y is a hydroxy group or a halogen atom is selectively removed, deprotection is preferably performed by an acid treatment. As an acid to be used for the deprotection, trifluoroacetic acid (hereinafter to be referred to as TFA), hydrochloric acid, sulfuric acid, methanesulfonic acid, p-toluenesulfonic acid and the like can be mentioned, with preference given to TFA. As a solvent to be used for the deprotection, for example, chloroform, dichloromethane, 1,2-dichloroethane or a mixed solvent thereof and the like can be mentioned. The concentration of an acid to be used for the deprotection is, for example, 0.1 w/v %-5 w/v %.

It is also possible to remove an anchor group derived from an anchor of the aforementioned formula (I) wherein Y is a hydroxy group, an —NHR group, or a halogen atom, simultaneously with the protecting group of other side chain in a peptide. In this case, a conventional method used in the field, particularly peptide synthesis, is used, and a method including adding an acid and the like is preferably used. As the acid, TFA, hydrochloric acid, sulfuric acid, mesylic acid, tosylic acid, trifluoroethanol, hexafluoroisopropanol and the like are used. Of these, TFA is particularly preferable. The amount of the acid to be used is appropriately set according to the kind of the acid to be used, and an amount suitable for removing the anchor group is used. The amount of the acid to be used is preferably not less than 3 mol, more preferably not less than 5 mol, preferably not more than 100 mol, more preferably not more than 50 mol, per 1 mol of the C-protected peptide. Along with such use, trifluoromethanesulfonic acid, trimethylsilyl trifluoromethanesulfonate, $BF_3$.etherate and the like can also be added as a further source of strong acid.

While the reaction temperature is not particularly limited as long as the reaction proceeds, for example, it is 0° C.-50° C., preferably 0° C.-30° C. The reaction time is, for example, 0.5-24 hr.

For confirmation of the progress of the reaction in the above-mentioned steps (a), (2), (4) and (5), a method similar to general liquid phase organic synthetic reaction can be applied. That is, thin layer silica gel chromatography, high performance liquid chromatography and the like can be used to trace the reaction.

EXAMPLES

The present invention is explained in more detail in the following by referring to Reference Example and Experimental Examples, which are not to be construed as limiting the scope of the present invention in any way. The reagents, apparatuses and materials used in the present invention are commercially available unless otherwise specified. In the present specification, when amino acid and the like are indicated by abbreviations, each indication is based on the abbreviation of the IUPAC-IUB Commission on Biochemical Nomenclature or conventional abbreviations in the art.

The anchor used in the Experimental Example can be produced by a method known per se (see the aforementioned patent documents 1-6, non-patent document 1) or a method analogous thereto, or method according to the following Reference Example 1, from a known starting material compound (or commercially available product).

Reference Example 1

Synthesis of 4-methoxy-2-[3',4',5'-tri(octadecyloxy) benzyloxy]benzyl alcohol (anchor (A))

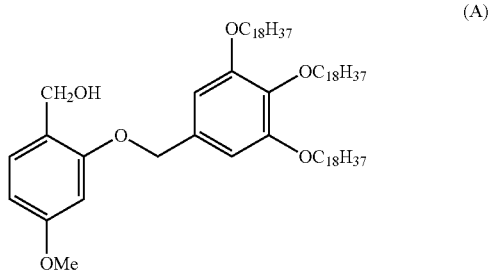

(i) 3,4,5-Tri(octadecyloxy)benzyl alcohol (83.0 g, 90.8 mmol) was dissolved in chloroform (830 ml), thionyl chloride (21.6 g, 0.182 mol) was added at 0° C. and the mixture was stirred for 1.5 hr at room temperature. The solvent was evaporated, and the residue was crystallized from acetonitrile (800 ml) to give 3,4,5-tri(octadecyloxy)benzyl chloride as wet crystals (93.6 g).

(ii) 3,4,5-Tri(octadecyloxy)benzyl chloride (93.6 g, wet, <90.8 mmol), 2-hydroxy-4-methoxybenzaldehyde (15.2 g, 0.10 mol), potassium carbonate (31.4 g, 0.23 mol) were suspended in DMF (830 ml), and the mixture was stirred at 80° C. overnight. The reaction mixture was dissolved in chloroform (1600 ml), and washed three times with 1N hydrochloric acid (800 ml), once with 5 wt % aqueous sodium hydrogen carbonate solution (800 ml) and once with 20 wt % brine (800 ml). The solvent was evaporated, and the residue was crystallized from methanol (800 ml), and washed with acetonitrile (800 ml) to give 4-methoxy-2-[3',4',5'-tri(octadecyloxy)benzyloxy]benzaldehyde (93.5 g, 89.2 mmol, yield 98%).

(iii) 4-Methoxy-2-[3',4',5'-tri(octadecyloxy)benzyloxy]benzaldehyde (93.5 g, 89.2 mmol) was dissolved in THF-methanol (1870 ml+94 ml), and sodium borohydride (4.05 g, 107 mmol) was added at 0° C. After stirring at room temperature for 1.5 hr, 0.2N hydrochloric acid (100 ml) was added at 0° C. to quench the reaction. About half the solvent was evaporated, the residue was dissolved in chloroform (2400 ml) and washed two times with 0.1N hydrochloric acid (1200 ml), once with 5 wt % aqueous sodium hydrogen carbonate solution (1200 ml) and once with 20 wt % brine (1200 ml). The solvent was evaporated, and the residue was crystallized from methanol (900 ml), and washed with acetonitrile to give 4-methoxy-2-[3',4',5'-tri (octadecyloxy)benzyloxy]benzyl alcohol (anchor (A), 92.4 g, 88.0 mmol, yield 97% (vs 3,4,5-tri(octadecyloxy) benzyl alcohol)).

$^1$H-NMR (300 MHz, CDCl$_3$): δ 0.88 (9H, t, J=6.3 Hz, C$_{17}$H$_{34}$-Me), 1.15-1.40 (84H, br, C3', 4', 5'-OC$_3$H$_6$—C$_{14}$H$_{28}$—CH$_3$), 1.40-1.55 (6H, br, C3', 4', 5'-OC$_2$H$_4$—CH$_2$—C$_{15}$H$_{31}$), 1.70-1.85 (6H, m, C3',4',5'-OCH$_2$—CH$_2$—C$_{16}$H$_{33}$), 2.18 (1H, t, J=6.3 Hz, OH), 3.79 (3H, s, C4-OMe), 3.90-4.03 (6H, m, C3', 4', 5'-O—CH$_2$—C$_{17}$H$_{35}$), 4.65 (2H, d, J=6.6 Hz, Ar—CH$_2$—OH), 4.97 (2H, s, Ar—O—CH$_2$—Ar), 6.47 (1H, dd, J=2.1, 8.1 Hz, C5-H), 6.53 (1H, d, J=2.4 Hz, C3-H), 6.60 (2H, s, C2',6'-H), 7.19 (1H, d, J=8.1 Hz, C6-H)

Experimental Example 1

Comparison of Impurity Contents Due to Difference of Precipitation Solvent

Test Method:

Anchor (A) (500 mg) was dissolved in chloroform, and Fmoc-Phe-OH (1.3 equivalents), dimethylaminopyridine (0.15 equivalent), and EDC HCl (1.4 equivalents) were added to allow reaction. After completion of the reaction, diethylamine (15 equivalents) and DBU (2.5 equivalents) were directly added to the reaction solution to remove the Fmoc group, and the solution was neutralized with 4M HCl/CPME (2.5 equivalents). The solvent was evaporated under reduced pressure, and the residue was precipitated with acetonitrile alone or 80% water-containing acetonitrile, and the precipitate was filtered and slurry washed with acetonitrile. Wet crystals were dissolved in chloroform, condensed by adding Fmoc-His(Trt)-OH (1.1 equivalents), EDC HCl (1.2 equivalents) and HOBt (0.1 equivalents). In the same manner as above, the Fmoc group was removed, and precipitation was performed with acetonitrile alone (or 80% water-containing acetonitrile). The same operation was repeated and, after condensation with Fmoc-Gly, the Fmoc group was removed to give a tripeptide-protected product. The thus-obtained tripeptide-protected product was treated with TFA to remove the anchor group and the side chain functional group-protecting group. The content of impurity (e.g., double-hit compound etc.) formed other than the object product H-Gly-His-Phe-OH was compared between precipitation with acetonitrile alone and precipitation with 80% water-containing acetonitrile.

HPLC Measurement Condition

Measurement device: LC-20A manufactured by SHIMADZU CORPORATION

Column: YMC-Pack ODS-A 4.6×150 mm (5 μm)

Temperature: 40° C.

Wavelength: 220 nm

Flow rate: 1.0 ml/min

Eluent: SOLUTION A 0.05 v/v % TFA-water
SOLUTION B 0.05 v/v % TFA-MeCN

Time program: SOLUTION B concentration 0 min 1 v/v %
20 min 50 v/v %
25 min 50 v/v %

Experimental results: As shown in Table 1, when precipitation was repeated with acetonitrile alone, impurity was by-produced in a large amount (45 area % (area ratio relative to peak of object tripeptide in HPLC analysis data)), whereas when precipitation was repeated with 80% water-containing acetonitrile, impurity was scarcely formed.

TABLE 1

Quantitative ratio of impurity to final deprotected
product (peak area ratio: area %)

| | +Phe | +His | +PheHis | +PhePhe |
|---|---|---|---|---|
| acetonitrile | 20 | 17 | 3 | 5 |
| 80% water-containing acetonitrile | 0.3 | 0 | 0 | 0 |

+Phe: H-Gly-His-Phe-Phe-OH
+His: H-Gly-His-His-Phe-OH
+PheHis: H-Gly-His-Phe-His-Phe-OH
+PhePhe: H-Gly-His-Phe-Phe-Phe-OH

Experimental Example 2

Comparison of Amino Acid Removal Performance by Precipitation Solvent

Experimental Method:

Anchor (A), anchor (B) or anchor (C) shown below was dissolved in chloroform, and Fmoc-amino acid (hereinafter sometimes to be also indicated as "Fmoc-Xaa-OH") (1.2 equivalents), dimethylaminopyridine (0.1 equivalent), and EDC HCl (1.3 equivalents) were added to perform dehydration condensation. After the completion of the reaction, diethylamine (15 equivalents) and DBU (2 equivalents) were directly added to the reaction solution without isolation to remove Fmoc group, and the solution was neutralized by the addition of 4M HCl/CPME (2 equivalents). The solvent was evaporated under reduced pressure. Various solvents for exchange were added to the residue and the mixture was stirred, and the precipitate was collected by filtration, washed with the same solvent for exchange added to the residue and dried. The contents of the residual amino acid and protected amino acid (H-His(Trt)-OH) in the crude crystals of Xaa-O-anchor group (derived from anchor (A)) were measured by amino acid analysis and HPLC (Table 2).

The measurement conditions of HPLC are the same as those in Experimental Example 1. The measurement condition of amino acid analysis is as follows.
Measurement device: AAA (HITACHI L-8900)
Column: HITACHI #2622PH 4.6 mm×60 mm
HITACHI #2650L 4.6 mm×40 mm
Solvent: L-8500PH Kit
Temperature: 57° C.

In addition, the precipitates obtained by adding various solvents for exchange were dissolved in chloroform, Fmoc-Leu was added, and a condensation reaction was performed using EDC. HCl/HOBt. A small amount of the reaction solution was taken, and the content of a double-hit compound (Fmoc-Leu-Xaa-Xaa-OH) in crude Fmoc-Leu-Xaa-OH obtained by removing the anchor group (derived from the following anchor (A), (B) or (C)) in TFA was measured by HPLC under the same measurement conditions as in Experimental Example 1 (Table 3).

TABLE 2

Contents of residual amino acid and protected amino acid (H-His(Trt)-OH)
in crude crystals of Xaa-O-anchor group (derived from anchor (A))

| Xaa | Phe | Gly | Ile | His(Trt) |
|---|---|---|---|---|
| acetonitrile | 0.06 wt % | 0.04 wt % | 0.02 wt % | 1.6 wt % |
| 80% water-containing acetonitrile | 0.001 wt % | 0.01 wt % | 0.004 wt % | 0 |

TABLE 3

Content (area %) of double-hit compound
(Fmoc-Leu-Xaa-Xaa-OH) in crude Fmoc-Leu-Xaa-OH

| Anchor | Xaa | First residue amino acid (equivalents) | acetonitrile | 90% water-containing acetonitrile | 80% water-containing acetonitrile | 60% water-containing acetonitrile |
|---|---|---|---|---|---|---|
| (A) | Phe | 1.4 | 4.8 | 1.1 | 0 | 0.9 |
| (B) | | 1.4 | 6.7 | — | 0.1 | — |
| (A) | Gly | 1.2 | 4.5 | — | 0.7 | — |
| (B) | | 1.2 | 2.5 | — | 0.7 | — |
| (C) | | 1.4 | 4.7 | — | 0.5 | — |
| (A) | His | 1.2 | 2.0 | — | 0.1 | — |
| (B) | (Trt) | 1.4 | 1.5 | — | 0.1 | — |
| (C) | Lys (Boc) | 1.2 | 1.6 | — | 0.2 | — |

The anchors used in Experimental Example 2 were anchor (A) shown in Reference Example 1, anchor (B) shown by the formula:

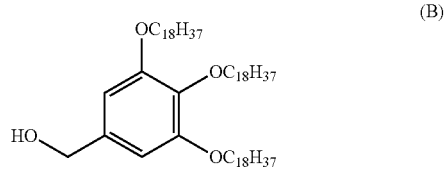

(B)

and anchor (C) shown by the formula:

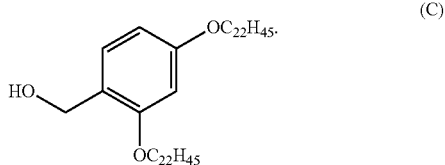

(C)

Experimental Results:

As shown in Table 2, it was found that the precipitation with 80% water-containing acetonitrile can efficiently remove residual amino acid as compared to the precipitation with acetonitrile alone. As shown in Table 3, moreover, it was found that the precipitation with water-containing acetonitrile within the range defined in the present invention (particularly, 80% water-containing acetonitrile) remarkably inhibits problematic by-production of a double-hit compound during peptide synthesis.

Experimental Example 3

Comparison of Amino Acid Removal Performance in Dipeptide Synthesis in Co-Presence of Various Fmoc-Amino Acids Experimental Method:

A synthesized and isolated Fmoc-Phe-O-anchor group (derived from the above-mentioned anchor (B) or (C)) was dissolved in chloroform, various Fmoc-amino acids (0.2 equivalents) were added to be mixed in the solution. To this solution were added DBU and diethylamine to remove the Fmoc group, a crude product of an H-Phe-O-anchor group was obtained by precipitation by the addition of various solvents for exchange, and condensed with Fmoc-Leu using EDC/HOBt. A small amount of the condensation reaction mixture was taken, and the anchor group was removed in TFA and the mixture was analyzed by HPLC, and a quantitative ratio of a double-hit compound of the amino acid mixed (Fmoc-Leu-Xaa-Phe) relative to the object dipeptide Fmoc-Leu-Phe was measured. The results are shown in Tables 4 and 5.

Experimental Results:

As shown in Tables 4 and 5, it was found that the precipitation with water-containing acetonitrile within the range defined in the present invention (particularly, 80% water-containing acetonitrile) remarkably inhibits by-production of a double-hit compound, as compared to the precipitation with acetonitrile alone or precipitation with 20% water-containing acetonitrile. It was also confirmed that 80% to water-containing acetonitrile shows less by-production of a double-hit compound as compared to water-containing acetone, water-containing DMF, water-containing methanol and water-containing ethanol, each having an acetonitrile content of 80 v/v %.

Industrial Applicability

According to the production method of peptide of the present invention, by performing precipitation and solid-liquid separation by the addition of particular water-containing acetonitrile after dehydration condensation of an N-terminal amino group of an amino acid or peptide having a C-terminal protected by an anchor group and a C-terminal carboxy group of an N-protected amino acid or N-protected peptide, and a subsequent removing step of an N-terminal temporary protecting group, a condensation step and an N-terminal deprotection step can be successively performed in one pot in a good yield. According to the present invention, complicated isolation and purification operations such as solvent evaporation after a condensation step, precipitation by solvent exchange, filtration, washing, drying and the like can be omitted, and by-production of a double-hit compound and the like

TABLE 4

| | | Quantitative ratio (area %) of double-hit compound (Fmoc-Leu-Xaa-Phe) | | | | | |
|---|---|---|---|---|---|---|---|
| Anchor | Xaa | 90% water-containing acetonitrile | 85% water-containing acetonitrile | 80% water-containing acetonitrile | 75% water-containing acetonitrile | 70% water-containing acetonitrile | 80% water-containing acetonitrile + methanol |
| (B) | Phe | 2.1 | 0.7 | 0.4 | 1.7 | 1.9 | — |
| | Gly | — | — | 0 | — | — | 1.6 |
| | His (Trt) | — | — | 0 | — | — | — |
| | Ile | — | — | 0.7 | — | — | — |
| | Lys (Boc) | — | — | 0.1 | — | — | — |
| | Gly-Gly | — | — | 0.2 | — | — | — |
| | Arg-Pro | — | — | 0 | — | — | — |
| (C) | Phe | 0.3 | 0.2 | 0.6 | 1.0 | 1.0 | — |
| | Gly | 1.4 | — | 0 | — | — | — |
| | His (Trt) | 1.7 | — | 0.1 | — | — | — |

Content of 80% water-containing acetonitrile in 80% water-containing acetonitrile + methanol: 95 v/v %

TABLE 5

| | | Quantitative ratio (area %) of double-hit compound (Fmoc-Leu-Xaa-Phe) | |
|---|---|---|---|
| Anchor | Xaa | acetonitrile | 20% water-containing acetonitrile |
| (B) | Phe | 3.1 | 4.1 |
| | Gly | 2.0 | 2.5 |
| | His(Trt) | 1.8 | 2.7 |
| | Ile | 1.9 | 4.9 |
| | Lys(Boc) | 1.1 | 2.2 |
| | Gly-Gly | 1.7 | — |
| | Arg-Pro | 1.5 | — |
| (C) | Phe | 4.1 | 4.3 |
| | Gly | 2.0 | 2.5 |
| | His(Trt) | 6.9 | 9.7 | is not found. Therefore, a convenient and efficient production method of peptide, which enables scaling up and is suitable for industrial production can be provided.

A differently expression method showing the characteristics of the production method of peptide of the present invention is described below.

An "immobilizing-protecting group" is defined as a "protecting group uninfluenced in a (deprotection step) and a (condensation step), and deprotected in a (final deprotection step)", and a general "protecting group" is defined as a "protecting group uninfluenced in a (condensation step), and deprotected in a (deprotection step)".

When a "production method of peptide by a method of immobilizing-protecting C-terminal and elongating N-terminal" is defined as a "production method of peptide comprising elongating a peptide chain in the N-terminal direction by repeating a step of condensing an amino acid or peptide having immobilized and protected C-terminal and a novel N-terminal protected amino acid or peptide (condensation step), and a step of N-terminal deprotection of the elongated N-terminal protected peptide having immobilized and protected C-terminal (deprotection step)", Fmoc method and Boc method are included therein, and the Fmoc method is preferable.

Here, when an "improved successive method of immobilizing-protecting C-terminal and elongating N-terminal" is defined as a "method of immobilizing-protecting C-terminal and elongating N-terminal characterized by successively performing a (condensation step) and a (deprotection step) in a solution without purification by extraction, precipitation and the like on the way between these steps and purifying by a (precipitation step) after the completion of the (deprotection step)", the production method of peptide of the present invention can also be expressed as follows.

[1] A production method of peptide by an improved successive method of immobilizing-protecting C-terminal and elongating N-terminal, comprising, after a deprotection step, a precipitation step in a polar solvent containing acetonitrile and water.

[2] The production method of peptide of [1], wherein the polar solvent is 60-95% water-containing acetonitrile.

[3] The production method of peptide of [1]] or [2], wherein the protecting group is an Fmoc group.

[4] The production method of peptide of any one of [1]-[3], further comprising a final deprotection step.

The production method of peptide of the present invention can be further expressed in detail as follows.

(The First Step: C-Terminal Immobilizing-Protecting Step)
A step of producing N-terminal protected amino acid or peptide with immobilized and protected C-terminal by reacting C-terminal of an N-terminal protected amino acid or peptide with an immobilizing-protecting group.

(The Second Step: Deprotection Step)
A step of producing amino acid or peptide with immobilized and protected C-terminal by removing the N-terminal protecting group of the N-terminal protected amino acid or peptide with immobilized and protected C-terminal.

(The Third Step: Condensation Step)
A step of producing elongated N-terminal protected peptide with immobilized and protected C-terminal by condensing amino acid or peptide with immobilized and protected C-terminal and a novel N-terminal protected amino acid or peptide.

(The Fourth Step: Deprotection Step)
A step of producing amino acid or peptide with immobilized and protected C-terminal by removing the N-terminal protecting group of the N-terminal protected amino acid or peptide with immobilized and protected C-terminal.

(The Fifth Step: Precipitation Step)
A step of purifying the elongated N-terminal protected peptide with immobilized and protected C-terminal by precipitating the elongated N-terminal protected peptide with immobilized and protected C-terminal in a polar solvent.

(The Sixth Step: Final Deprotection Step)
A step of producing an elongated peptide by removing the immobilized-protected C-terminal from the elongated N-terminal protected peptide with immobilized and protected C-terminal or elongated peptide with immobilized and protected C-terminal.

Since the above-mentioned third step, fourth step, and fifth step are repeated as one set, the production method of peptide of the present invention specifically includes the following case.

The first step→the second step→(the third step→the fourth step→the fifth step)×m times→the sixth step wherein m is a natural number, and "( . . . )×m times" means that the step in the parenthesis is repeated m times.

This application is based on a patent application No. 2011-122943 filed in Japan, the contents of which are incorporated in full herein.

The invention claimed is:

1. A method of producing a peptide, comprising:

(1) condensing an N-terminal amino group of (a) a C-protected amino acid or (b) a C-protected peptide, with a C-terminal carboxy group of (c) an N-protected amino acid or (d) an N-protected peptide in a solvent to obtain a reaction solution which comprises an (e) N-protected C-protected peptide, wherein a C-terminal carboxy group of said (a) C-protected amino acid or said (b) C-protected peptide is protected by an anchor group;

(2) removing the N-terminal protecting group of said (e) N-protected C-protected peptide in said reaction solution, without isolating said N-protected C-protected peptide from said reaction solution, to obtain (b') a C-protected peptide, wherein when said condensing is conducted with said (b) C-protected peptide, then said (b) C-protected peptide and said (b') C-protected peptide are different; and (3) precipitating said C-protected peptide in a solvent comprising a water-acetonitrile mixture, wherein said water-acetonitrile mixture comprises 60 to 95% v/v acetonitrile, based on the total volume of said mixture, after said (2) removing; and (4) obtaining said C-protected peptide by solid-liquid separation, wherein said anchor group is a group represented by formula (II):

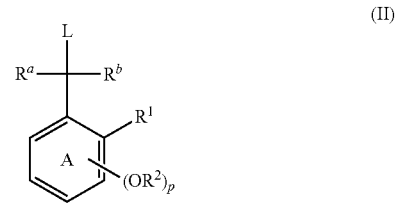

wherein:

$R^1$ is a hydrogen atom or, when $R^b$ is a group represented by the following formula (a), optionally forms a single bond together with $R^3$ to form a fluorene ring together with ring A and ring B;

each $R^2$ is independently an organic group having an aliphatic hydrocarbon group;

p is an integer of 1 to 4;

ring A optionally further has, in addition to $OR^2$, a substituent selected from the group consisting of a halogen atom, a $C_{1-6}$ alkyl group optionally substituted by a halogen atom, and a $C_{1-6}$ alkoxy group optionally substituted by a halogen atom;

R$^a$ is a hydrogen atom, or a phenyl group optionally substituted by a halogen atom; and R$^b$ is a hydrogen atom, or a group represented by formula (a):

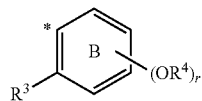

(a)

wherein:
* indicates the position of binding to the remainder of the molecule;
r is an integer of 0 to 4;
each R$^4$ is independently an organic group having an aliphatic hydrocarbon group;
R$^3$ is a hydrogen atom, or optionally forms a single bond together with R$^1$ to form a fluorene ring together with ring A and ring B; and
ring B optionally further has, in addition to OR$^4$, a substituent selected from the group consisting of a halogen atom, a C$_{1-6}$ alkyl group optionally substituted by a halogen atom, and a C$_{1-6}$ alkoxy group optionally substituted by a halogen atom; and
L represent a connection to the carbonyl group of said C-terminus and is —O— or —N(R)—, wherein R is a hydrogen atom, an alkyl group, or an aralkyl group.

2. The method according to claim 1, further comprising:
(5) removing the C-terminal anchor group of said (b') C-protected peptide after said (4) obtaining.

3. The method according to claim 1, wherein, in formula (II), R$^1$ is a hydrogen atom, R$^2$ and/or R$^4$ are/is aliphatic hydrocarbon group(s) having 5 to 60 carbon atoms, p is an integer of 1 to 3, and r is an integer of 0-2.

4. The method according to claim 1, wherein, in formula (II), R$^a$, R$^b$, and R$^1$ are each a hydrogen atom, R$^2$ is an aliphatic hydrocarbon group having 5 to 60 carbon atoms, and p is an integer of 1 to 3.

5. The method according to claim 1, wherein, in formula (II), R$^a$, R$^b$, and R$^1$ are each a hydrogen atom, R$^2$ is an alkyl group having 10 to 40 carbon atoms, and p is 2 or 3.

6. The method according to claim 1, wherein, in formula (II), R$^a$, R$^b$, and R$^1$ are each a hydrogen atom, R$^2$ is an alkyl group having 12 to 30 carbon atoms, and p is 2 or 3.

7. The method according to claim 1, wherein said anchor group is derived from an anchor compound selected from the group consisting of:
3,4,5-tri(octadecyloxy)benzyl alcohol,
2,4-di(docosyloxy)benzyl alcohol,
4-methoxy-2-[3',4',5'-tri(octadecyloxy)benzyloxy]benzyl alcohol,
4-methoxy-2-[3',4',5'-tri(octadecyloxy)cyclohexyl-methyloxy]benzyl alcohol,
2-methoxy-4-[3',4',5'-tri(octadecyloxy)cyclohexyl-methyloxy]benzyl alcohol,
4-[3',4',5'-tri(octadecyloxy)cyclohexylmethyloxy]benzyl alcohol,
3,5-dimethoxy-4-[3',4',5'-tri(octadecyloxy)cyclohexyl-methyloxy]benzyl alcohol,
2,4-di(dodecyloxy)benzyl alcohol,
3,4,5-tri(octadecyloxy)benzylamine,
bis(4-docosyloxyphenyl)methanol, and
bis(4-docosyloxyphenyl)methylamine.

8. The method according to claim 1, wherein said mixture comprises acetonitrile in an amount of 70 v/v% to 90 v/v% based on the the total volume of said mixture.

9. The method according to claim 1, wherein said mixture comprises acetonitrile in an amount of 75 v/v% to 85 v/v% based on the total volume of said mixture.

10. The method according to claim 1, wherein said mixture comprises acetonitrile in an amount of 80 v/v% based on the total volume of said mixture.

11. The method according to claim 1, wherein said solvent comprising a water-acetonitrile mixture is a mixed solvent of said water-acetonitrile mixture, and at least one solvent selected from the group consisting of methanol, ethanol, dimethylformamide, propionitrile, dimethyl sulfoxide, acetone, dichloromethane, chloroform, tetrahydrofuran, cyclopentyl methyl ether, and ethyl acetate.

12. The method according to claim 1, wherein said solvent is said water-acetonitrile mixture.

13. The method according to claim 1, wherein said amino-protecting group of said (c) N-protected amino acid or said (d) N-protected peptide is a 9-fluorenylmethyloxycarbonyl group, a tert-butoxycarbonyl group, or a benzyloxycarbonyl group.

14. The method according to claim 1, wherein the number of amino acid residues of said N-protected peptide is not more than 100.

15. The method according to claim 1, wherein the number of amino acid residues of said N-protected peptide is not more than 50.

16. The method according to claim 1, wherein the number of amino acid residues of said N-protected peptide is not more than 30.

17. The method according to claim 1, wherein the number of amino acid residues of said N-protected peptide is not more than 10.

18. The method according to claim 1, wherein the number of amino acid residues of said N-protected peptide is not more than 5.

19. The method according to claim 1, wherein the number of amino acid residues of the C-protected peptide is not more than 100.

20. The method according to claim 1, wherein the number of amino acid residues of the C-protected peptide is not more than 50.

21. The method according to claim 1, wherein the number of amino acid residues of the C-protected peptide is not more than 30.

* * * * *